United States Patent
Shea et al.

(12)

(10) Patent No.: US 6,525,154 B1
(45) Date of Patent: Feb. 25, 2003

(54) MOLECULAR IMPRINTING FOR THE RECOGNITION OF PEPTIDES IN AQUEOUS SOLUTION

(75) Inventors: Kenneth J. Shea; Bradley R. Hart, both of Irvine, CA (US)

(73) Assignee: The Regents of the University of California, Oakland, CA (US)

( * ) Notice: Subject to any disclaimer, the term of this patent is extended or adjusted under 35 U.S.C. 154(b) by 42 days.

(21) Appl. No.: 09/910,451

(22) Filed: Jul. 20, 2001

Related U.S. Application Data

(60) Provisional application No. 60/219,599, filed on Jul. 20, 2000.

(51) Int. Cl.[7] ............................................. C08F 120/54
(52) U.S. Cl. ..................... 526/307.2; 526/172; 526/199; 526/217; 526/220; 526/238.1; 526/306
(58) Field of Search ..................... 424/78.37; 526/172, 526/199, 217, 220, 238.1, 306, 307.2

(56) References Cited

U.S. PATENT DOCUMENTS 5,630,978 A * 5/1997 Domb ........................ 264/330
6,217,901 B1 * 4/2001 Perrott et al. ............... 424/450

* cited by examiner

*Primary Examiner*—Helen L. Pezzuto
(74) *Attorney, Agent, or Firm*—Roberts D. Buyan; Stout, Uxa, Buyan, Mullins, LLP

(57) ABSTRACT

Molecularly imprinted polymers (MIPs) wherein the template comprises either a) a peptide or amino acid sequence that has an N-terminal histidine residue or b) histamine. The MIP's may be prepared in aqueous systems using reagents that are water soluble at the relevant concentrations. Also, the invention includes methods for using the MIP's as receptors or adsorbents for, or to determine the present or non-presence of, target molecules containing i) particular peptides or amino acid sequences having N-terminal histidine residue or ii) histamine.

18 Claims, 7 Drawing Sheets

MOLECULAR IMPRINTING FOR THE RECOGNITION OF PEPTIDES IN AQUEOUS SOLUTION

RELATED APPLICATION

This patent application claims priority to abandoned United States Provisional Patent Application Serial No. 60/219,599 entitled "Selective Binding And Transport Of Peptides" filed on Jul. 20, 2000, the entirety of which is expressly incorporated herein by reference.

FIELD OF THE INVENTION

The present invention relates generally to chemical compositions and methods for recognizing, attracting, adsorbing, isolating or selectively binding certain chemical compounds. More particularly, the present invention relates to the preparation of molecularly imprinted polymer (MIP) compositions and the use of such MIP compositions as selective adsorbents for peptides and other compounds that contain amino acid sequences having at least one N-terminal histidine residue or for histamine.

BACKGROUND OF THE INVENTION

Molecular imprinting is a process for synthesizing materials that contain highly specific recognition sites for smaller molecules. Molecular imprinting techniques have generally been in use since the early 1970's, when it was first demonstrated that a highly crosslinked organic network polymer could serve as a scaffold for the molecular imprinting of a template of an organic molecule. Today, molecular imprinting is used for many purposes, including the creation of macromolecular binding and catalytic sites and as binding sites for the separation or resolution of optical isomers or enantiomers. See, Hart, B. R., Rush, D. J. and Shea, K. J., *Discrimination between Enantiomers of Structurally Related Molecules: Separation of Benzodiazepines by Molecularly Imprinted Polymers*, J. Am. Chem. Soc. Vol. 122, pp. 460–465 (2000).

The preparation of a MIP generally involves polymerizing functional monomers and crosslinking agents in the presence of a "template" compound. For example, a molecularly imprinted polymer may be prepared by polymerizing a mixture that contains a template compound, one or more polymerizable functional monomers, crosslinking agent(s), solvent(s), and a free radical initiator. Prior to polymerization, the monomer molecules distribute themselves around the template molecule in accordance with the size, polarity and functionality of the template molecule. As the polymerization reaction progresses, a rigid, three-dimensional polymer network is formed about the template. The template is removed, leaving an "imprint" or region in the polymer network that is complementary in size, shape, and functional group orientation to the template molecule.

More specifically, two general approaches have heretofore been developed for the preparation of MIPs. In one approach, the template is covalently bound to a polymerizable monomer and, after the polymerization has been completed, the covalent bond is cleaved so as to release the template from the polymer network. In the other approach, polymerizable monomers arrange themselves about a template based on noncovalent attractions or interactions (e.g., H-bonding, hydrophobic, ionic, steric or electrostatic interactions) and thereafter, after the polymerization has been completed, the non-covalently bound template is extracted, leached out or removed from the polymer network.

Molecular imprinting has proven to be useful in various applications, including chiral stationary phases (CSPs); as antibody mimics; as catalysts in organic synthesis; as mimics for particular enzymes and as biosensors in which the molecularly imprinted polymers are used as substitutes for other biological molecules.

In many of the methods previously known for preparation of MIPs, the monomers used have not been soluble in water or aqueous media at the concentrations utilized in the polymerization reaction. Since the use of an aqueous environment is desirable in many MIP preparations, such as where a MIP is prepared to be imprinted for a peptide or identifying segment of a peptide, there remains a need in the art for the development of new processes for aqueous-based preparation of MIPs.

SUMMARY OF THE INVENTION

The present invention provides methods for preparing molecularly imprinted polymer wherein the template comprises a peptide or amino acid sequence that has an N-terminal histidine residue or histamine. The method of the present invention generally comprises the steps of:

(A) providing a template complex that has the general formula

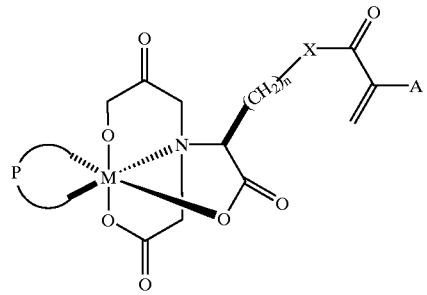

wherein M is nickel, cobalt, copper, zinc, lead or manganese, P is a template peptide or amino acid sequence having at least one N-terminal histidine or a histamine molecule, n=0 through 10, X is NH, O, S or is absent and A is H or alkyl;

(B) polymerizing the template complex provided in Step A with at least a first monomer and optionally said first monomer and a second monomer, to form a polymer network containing the template complex;

the first monomer having the general formula

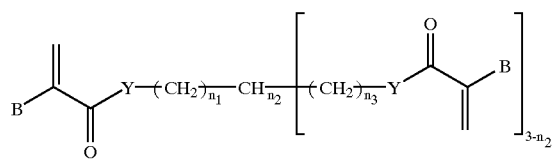

wherein Y is NH, O or S or is absent, $n_1$=0 through 10, $n_2$=0 through 2, $n_3$=0 through 10 and B is H or alkyl and the second monomer, if used, having the general formula

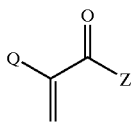

wherein Z=NH$_2$, OH, O—(CH$_2$)$_n$ wherein n=2 through 4, NH(alkyl) or N(alkyl)$_2$ and Q is H or alkyl.

After the polymerization is complete, the template complex may be removed from the polymer network, leaving the molecularly imprinted polymer network in tact.

Further in accordance with the present invention, the template complex, monomer(s) and reagents used in the above method may be soluble in water at the concentrations used in the method.

Still further in accordance with the present invention, the template complex provided in Step A may be prepared by combining a polymerizable methacrylamide-NTA-Ni$^{2+}$ complex with a peptide or an amino acid sequence having at least one N-terminal histidine or histamine. The polymerizable methacrylamide-NTA-Ni$^{2+}$ complex may be prepared by reacting NTA with NiSO$_4$ or any other suitable Ni(II) source.

Still further in accordance with the invention, the first monomer used in Step B may comprise N,N'-ethylene bisacrylamide or N,N'-methylene bisacrylamide.

Still further in accordance with the present invention, the optional second monomer (if used in Step B) may comprise a water soluble acrylamide, such as acrylamide or methacrylamide.

Still further in accordance with the present invention, there are provided methods and compositions for adsorbing a target compound that contains a predetermined amino acid sequence having at least one N-terminal histidine. These methods generally comprise the steps of i) providing a molecularly imprinted polymer prepared according to the method set forth hereabove in this summary of the invention, wherein the amino acid sequence used to prepare the template complex in Step A is the predetermined amino acid sequence and ii) contacting the molecularly imprinted polymer with the material such that the target compound contained in the material will be adsorbed by the molecularly imprinted polymer.

Still further in accordance with the present invention, there are provided methods and compositions for determining whether a material contains a target compound that contains a predetermined amino acid sequence having at least one N-terminal histidine. These methods generally comprise the steps of i) providing a molecularly imprinted polymer that has been prepared according to the method of this invention as set forth hereabove in this summary of the invention, wherein the wherein the amino acid sequence used to prepare the template complex in Step A is the predetermined amino acid sequence, ii) contacting the molecularly imprinted polymer with the material such that any substantial quantity of target compound within the material will be adsorbed by the molecularly imprinted polymer and, thereafter, iii) determining whether the molecularly imprinted polymer has adsorbed any of the target compound.

Still further in accordance with the present invention, there are provided molecularly imprinted polymer compositions that have been prepared by the method of the present invention as set forth hereabove in this summary of the invention and examples of which are described in detail herebelow.

Still further aspects and advantages of the present invention will become apparent to those of skill in the art upon reading the detailed descriptions of examples and embodiments, set forth herebelow.

DETAILED DESCRIPTIONS OF SPECIFIC EMBODIMENTS

Figure 1:
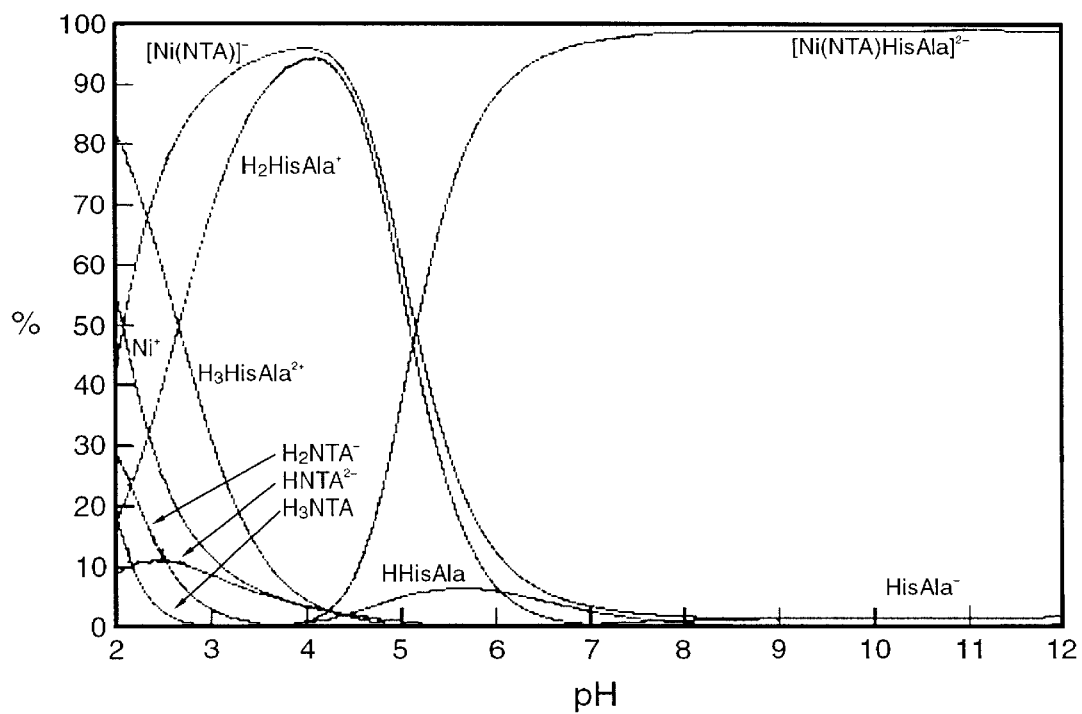
FIG. 1 is a graphic showing species distributions of a 0.01 M solution of His-Ala, Ni(II), and NTA ligand for pH values ranging from 2 to 12.

The following detailed descriptions and the accompanying figures, tables and diagrams are provided to describe certain examples or embodiments of the invention only and are not intended to exhaustively describe all possible examples or embodiments of the invention. This invention is in no way limited to only the specific embodiments and examples described in detail herebelow.

The preparation of artificial receptors or selective adsorbents capable of sequence selective recognition of short peptides has been a long-standing goal for many researchers working in the area of molecular recognition. Oligopeptides themselves are important targets for recognition, and often have significant physiological activity, they also represent an intermediate step toward the recognition of proteins, and protein surfaces.

One example of the present invention is a method for preparing receptors or selective adsorbents for peptides having affinity of N-terminal histidine residues for Ni(II). In these embodiments, a template complex is prepared from Ni(II), a polymerizable ligand, and an N-terminal histidine peptide. This template complex is then copolymerized with other hydrophilic monomers. Subsequent removal of the template peptide leaves behind a region within the polymer that is complementary to the template peptide in size and which contains a Ni(II) complex positioned to bind a N-terminal histidine. By incorporating a Ni(II) complex into the polymer, a handle is provided to bind peptides containing N-terminal histidine residues in water with high affinity.

Ni(II)-nitrilotriacetic acid (NTA) complex has previously been used as an adsorbent for protein purification. This ligand occupies four positions in the octahedral coordination sphere of Ni(II), leaving the remaining two for selective interactions. In addition to its use in metal affinity chromatography, the [Ni(NTA)]⁻ complex has been used in a wide variety of systems for the biofunctionalization of interfaces and for the selective recognition of His-tagged proteins.

NTA forms stable 1:1 complexes with Ni(II) with an association constant of over $10^{11}$. Histidine has been shown to bind to these complexes at the terminal amine and pyridine nitrogen of the imidazole ring with high affinity (Table 1). In addition, histidine and NTA are known to form 1:1:1 mixed complexes with several divalent metals with varying affinities (Table 1). The orbitals of octahedral ($d^8$) Ni(II) are hybridized as $sp^3d_z^2d_{x^2-y^2}$. This results in two unpaired electrons making these complexes paramagnetic.

Although other divalent metals such as copper, zinc or cobalt may be useable in this invention, nickel provides the highest association constant for the primary interaction, binding of N-terminal histidine residues to [Ni(NTA)]⁻ (Table 1). In addition, previous reports dealing with the incorporation of Cu(II) complexes into network polyacrylamides have demonstrated poor polymer yields, presumably due to inhibition of in the free radical polymerization by the copper. The oxidation of polyacrylamide radicals by Cu(II) in aqueous solution is a facile process. This is perhaps due to the low redox potential for the Cu(II)-Cu(I) couple (0.2 V). However, other metals with higher redox potentials, such as Fe(III), are also efficient at oxidizing acrylamide radicals.

TABLE 1

Dissociation constants for complexation of Histidine with various divalent metal-NTA complexes.

| Metal | $K_d^{a,b}$ (mM) |
|---|---|
| $Ni^{2+}$ | 0.0093 |
| $Cu^{2+}$ | 0.030 |
| $Zn^{2+}$ | 0.112 |
| $Co^{2+}$ | 0.114 |
| $Mn^{2+}$ | 3.23 |
| $Pb^{2+}$ | 31.6 |

[a] All association constants determined by potentiometric titrations. [b] I = 0.1M (NaClO₄).

Covalent incorporation of a polymer bound Ni(NTA) complex to bind N-terminal histidine peptides necessitates the development of a polymerizable form of the NTA ligand. The synthesis of methacrylamide functionalized NTA monomer 4 is shown in Scheme 1. This sequence begins with commercially available N-Cbz-L-lysine methyl ester (1). Bis-alkylation of the -nitrogen of 1 with ethylbromoacetate in the presence of potassium carbonate provided triester 2. Deprotection of the -nitrogen by hydrogenolysis, followed by acylation with methacryloyl chloride, give amide 3. Saponification of the amide 3 with lithium hydroxide in acetone/water (3:1) provides triacetate 4.

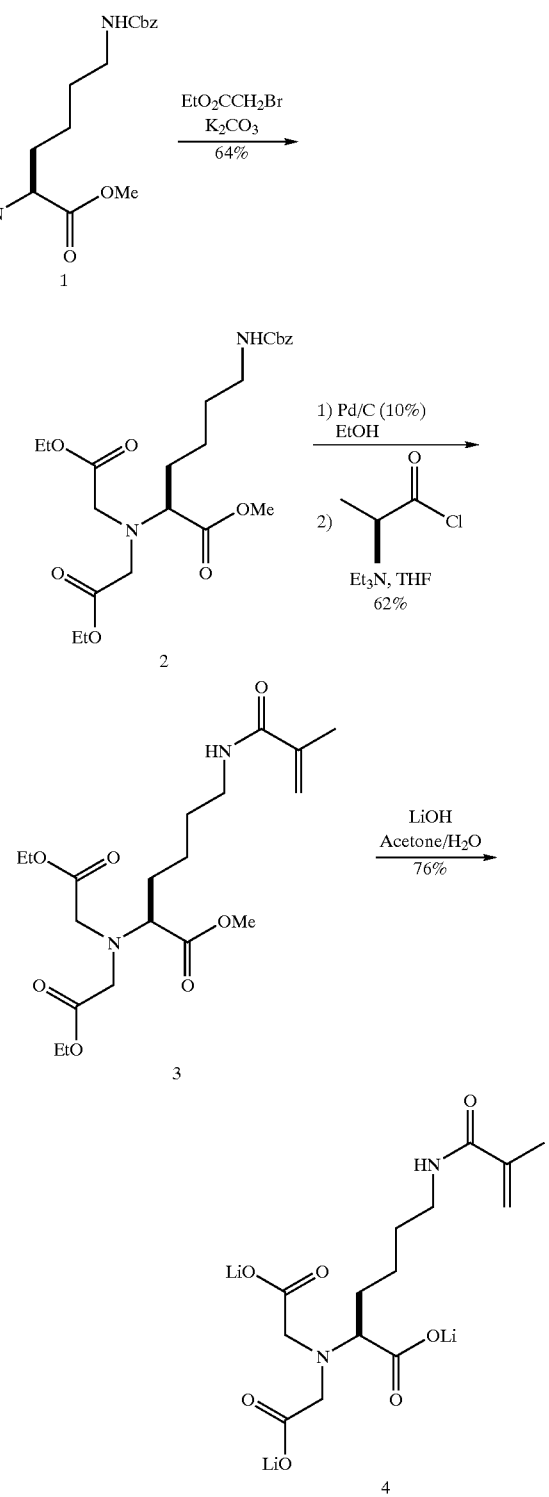

Scheme 1
Synthesis of NTA-methacrylamide ligand 4.

The polymerizable mixed complex [Ni(NTA)His-Ala]²⁻ (5) was prepared by combining equimolar aqueous solutions of NTA ligand, NiSO₄.6H₂O or Ni(NO₃)₂.6H₂O and histidine ligand (Scheme 2). The pH of the complex solution was then adjusted to approximately pH 7.5 with 0.1 N NaOH. Confirmation of the octahedral geometry of 5 was made by comparing the electronic spectra for 5 with the known absorbance bands for octahedral complexes of Ni(II). Due to the paramagnetic nature of the metal center, NMR was not useful for characterizing the complex. However, additional evidence for the formation of 5 was obtained by negative-ion electrospray mass spectroscopy. Peaks corresponding to the lithium salt of complex 5 were observed (m/z=546). In addition, peaks corresponding to [Ni(NTA)]$^-$ were observed (m/z=385). The relative ratio of 5 to [Ni(NTA)]$^-$ in the mass spectrum was approximately 10:1.4.

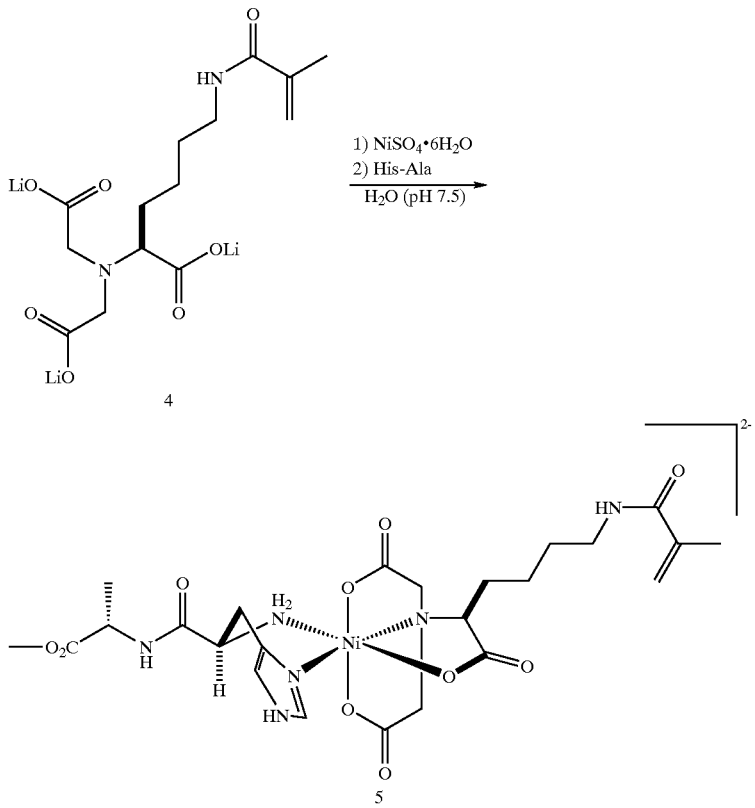

There are geometrical constraints placed on the positions of the donor atoms associated with each of the two ligands in 5, due to the conformations available to these molecules. The two nitrogen donors of histidine must be cis, and the three oxygen donors of the NTA ligand must be meridional. Even with these constraints, there are several possible isomers possible. These isomers can be divided into two main groups; those with the imidazole nitrogen of histidine cis to the NTA nitrogen, and those with it trans. For each of these two groups, there are three possible orientations of the chiral center-bearing acetate of the NTA ligand with respect to the chiral center on histidine. This equates to a total of six possible diastereomers for complex 5.

The formation of the mixed complex of Ni(II), polymerizable NTA ligand 4 and His-Ala was evaluated potentiometrically and its formation constant was calculated. Similar formulations may utilize a mixed complex of histidine, NTA and Ni(II). However, the formulations wherein such mixed complex is used differ from that the above-set-forth example in at least two ways. First, the NTA ligand may be modified to include a polymerizable "tail." Second, N-terminal histidine peptides may be used as ligands instead of histidine alone. It was not known what effect, if any, these changes would have on complex formation. These studies will permit identification of the dominant species in solution at various pH values. Additionally, these titrations will be used as a baseline for future potentiometric titrations, which will be performed on polymeric (homogeneous and heterogeneous) systems.

All titrations were carried out using 1.00 N KOH under $N_2$ in a 10 mL jacketed vessel at 25.0±0.1° C. The ionic strength of the solution was maintained at 0.1 M with $KNO_3$.

All equilibrium constants were calculated using the computer program Best 7. All details of this type of analysis have been previously described. Species distribution curves were obtained from the computer program SPE.[15-18] The log of the formation constant for this 1:1:1 complex was calculated from this data (log $K_f$=5.8, Table 2). This compares to the literature value for the association of histidine with [Ni(NTA)]$^-$ of log $K_f$=5.03.

TABLE 2

Calculated formation constant for [Ni(NTA)HisAla]$^{2-}$ and literature values for the formation constants of [Ni(NTA)His]$^{2-}$ and [Ni(NTA)]$^-$.

| | log $K_f$ |
|---|---|
| [Ni(NTA)HisAla]$^{2-}$ | 5.80 |
| [Ni(NTA)His]$^{2-}$ | 5.03[a] |
| [Ni(NTA)]$^-$ | 11.5[a] |

[a]Literature values from Ref. 5.

FIG. 1 shows species distributions for a 0.01 M solution of His-Ala, Ni(II), and NTA ligand 4 for pH values ranging from 2 to 12. This diagram shows the maximum formation of the 1:1:1 complex at pH>7.0. There are no other metal containing species present at this pH. Other species present at lower pH values include [Ni(NTA)]⁻ and diprotonated His-Ala. Both species reach a maximum concentration at pH 4.0.

These results indicate that the dipeptide His-Ala has an association constant comparable to histidine for complexation to [Ni(NTA)]⁻. In addition, the modifications were made to the NTA ligand do not appear to have a detrimental effect on the formation of the 1:1:1 complex.

Polymer Synthesis

In some embodiments of the invention where AIBN (1 mol %) may be used as the polymerization initiator, but a temperature of at least about 65° C. is required. In addition, a small amount of methanol is needed to dissolve the AIBN. However, when it is desired to lower the temperature required for the polymerization and to eliminate the use of any cosolvents, a redox initiator system of N,N'-tetramethylethylenediamine (TMEDA) and ammonium persulfate (APS) may be employed (Scheme 3). This initiator system is water soluble and is efficient at much reduced temperatures and concentrations when compared to AIBN. For example, in embodiments of the present invention, the amount of initiator may be reduced from 1 mol % for AIBN to 0.02 mol % and 0.10 mol % for TMEDA and APS respectively. While persulfate itself is an effective initiator, the rate of polymerization may increase approximately three-fold in the presence of TMEDA. Gel times for the polymerization shown in Scheme 3 range from approximately 10 min to 30 min depending on the amount of cross-linking monomer used.

Scheme 3
Synthesis of EBA cross-linked polyacrylamides P-1-P-10.
Pep = amino acid sequence appended to histidine.

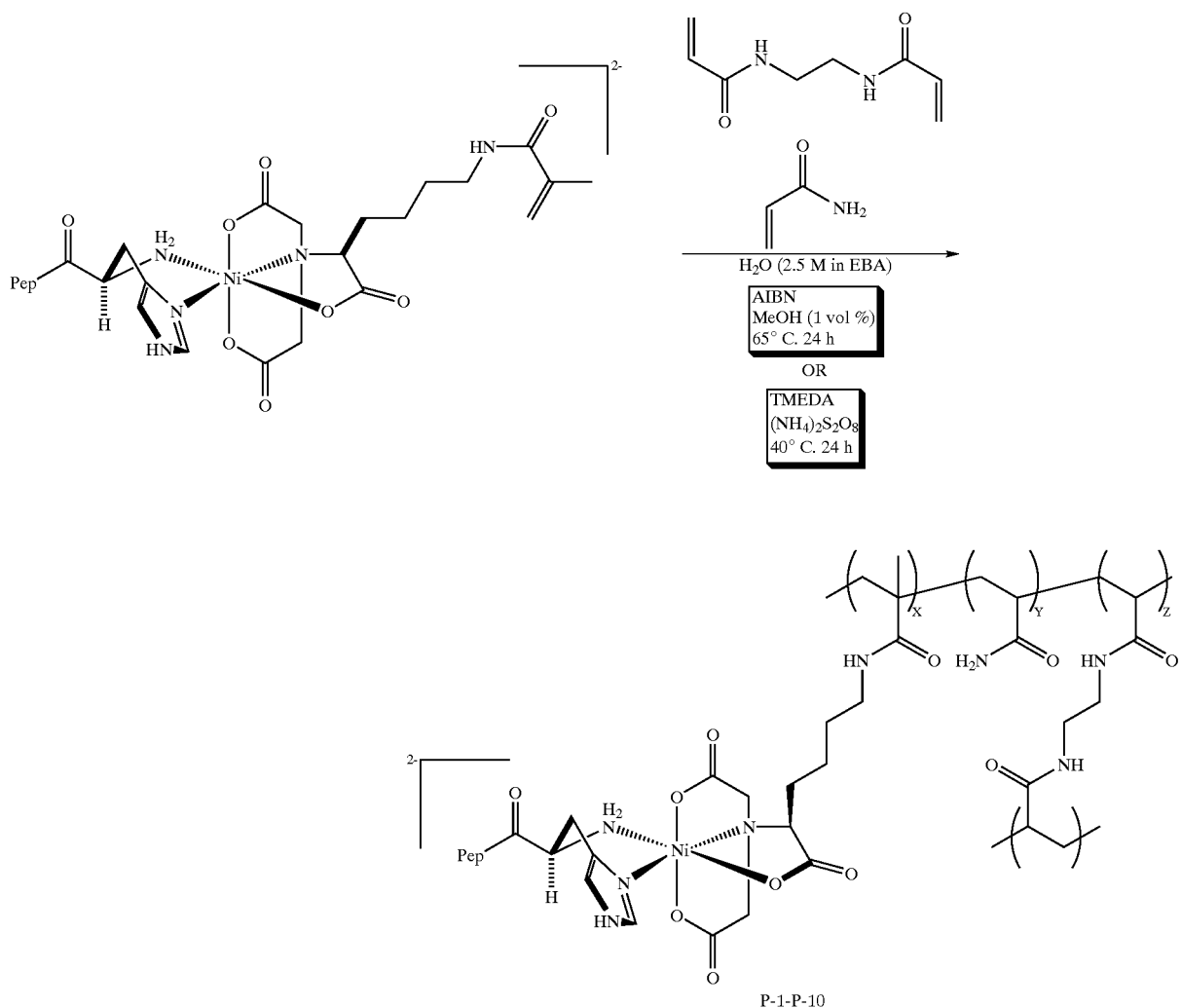

Table 3 contains the formulations for several polymers prepared with varying amounts of cross-linking monomer. As shown in Table 3, in addition to changing the initiator system, the total loading of template complex may be reduced to 2 mol %. By reducing the total amount of $Ni^{2+}$ bound to the polymer, the amount of template required for each polymerization is reduced. This also aids in achieving binding site homogeneity by limiting the possibility of cooperative binding by two metal centers. The polymers in Table 3 have all been obtained in quantitative yield, with the exception of P-7. This polymer never formed a homogeneous gel; rather, the forming polymer precipitated, leaving a significant volume of supernatant solution, which contained large amounts of unreacted monomers. Because of this, polymer P-7 was omitted from our binding studies.

TABLE 3

Polymerization formulation composition for the synthesis of EBA cross-linked polymer P-1 through P-7.

| Polymer | Template Peptide | NTA Complex | Acrylamide | EBA |
|---|---|---|---|---|
| P-1 | His-Ala | 2 | 20 | 80 |
| P-2 | His-Ala | 2 | 28 | 70 |
| P-3 | His-Ala | 2 | 38 | 60 |
| P-4 | His-Ala | 2 | 48 | 50 |
| P-5 | His-Ala | 2 | 58 | 40 |
| P-6 | His-Ala | 2 | 68 | 30 |
| P-7 | His-Ala | 2 | 88 | 10 |

Polymer Formulation Components (mol %)

The resulting polymers had textures and physical consistencies that varied depending on the cross-link level. At a low (30%) cross-link level, the polymers were very rubbery when wet. When dried, this polymer became extremely tough and difficult to grind into small particles. At higher cross-linking levels, the materials became less rubbery and were more brittle in the dry state.

The polymers were ground and washed with water (pH= 3-4) to remove the template. Following the acidic wash, the polymer was washed with a solution of 0.02 M $Ni(SO_4)$. $6H_2O$ to replace any nickel lost during the acidic wash. The splitting yield was quantified by combining the acid wash fractions and determining the concentration of histidine by HPLC. For polymers P-1 through P-6, template peptide recovery was greater than 90%. The polymer particles were wet sieved and those particles sized between 38 and 425 m were used for binding.

Binding isotherms were obtained for N-terminal histidine peptide binding to each polymer at several concentrations. $B_{max}$ was determined by fitting the isotherm data to a one-site binding model. In order to accurately compare the values of $B_{max}$ for each polymer, it was necessary to normalize the binding data with respect to the nickel content of the polymer. This was necessary for two reasons. First, there is some natural variation in nickel content between polymer batches. Second, the polymers are prepared using a mole ratio for the monomers; therefore, the wt % nickel for each of the polymers will not be the same even though the mol % should be similar. The theoretical values of nickel content can be calculated. However, the nickel content determined by elemental analysis was consistently lower than the theoretical value. Therefore, for each polymer the amount of bound peptide was normalized against the nickel content based on elemental analysis. This normalization manifests itself as binding being expressed as mol of bound peptide divided by mol of nickel (mol bound/mol Ni). This allows for direct comparison of the peptide uptake observed with these polymers.

Figures 2A, 2B, 2C, 2D:
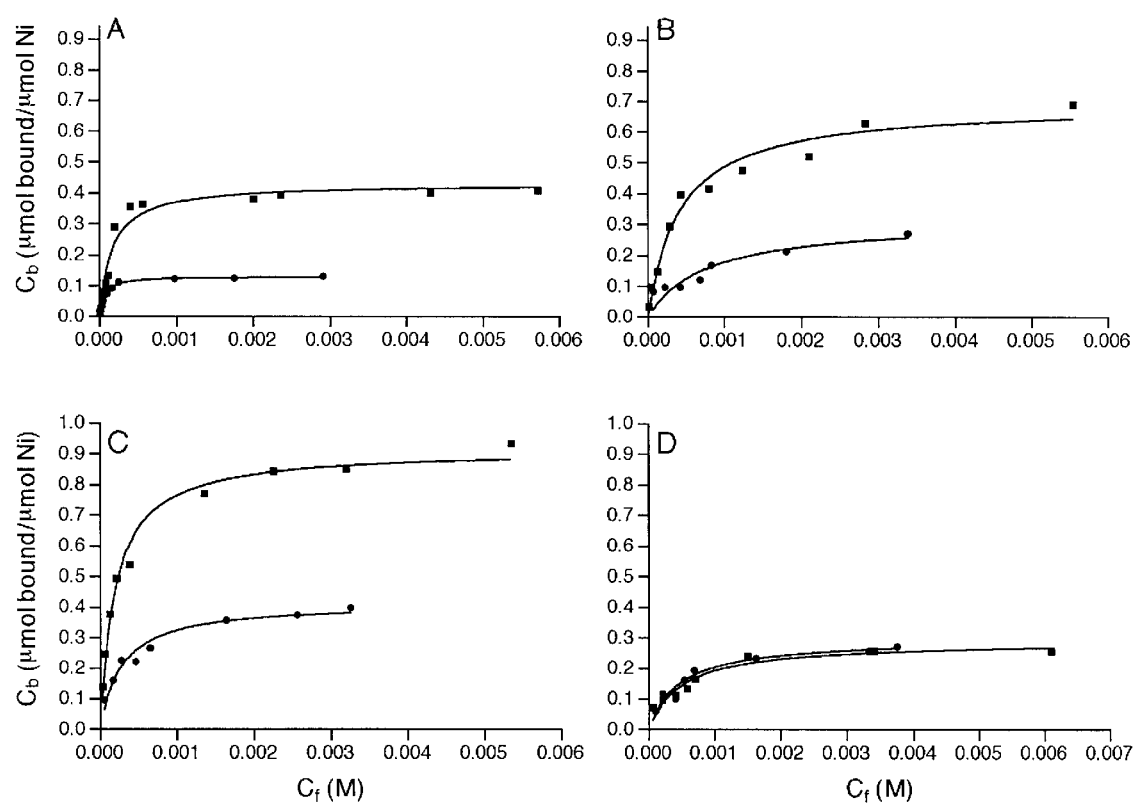
FIG. 2a is a graphic showing the binding isotherm for a particular 80% cross-linked MIP of the present invention.
FIG. 2B is a graphic showing the binding isotherm for a particular 70% cross-linked MIP of the present invention.
FIG. 2C is a graphic showing the binding isotherm for a particular 50% cross-linked MIP of the present invention.
FIG. 2D is a graphic showing the binding isotherm for a particular 30% cross-linked MIP of the present invention.

Binding isotherms for template His-Ala and His-Phe binding to P-1–P-6 are shown in FIGS. 2a, 2b, 2c and 2d, wherein data points for His-Ala are indicated by the symbol (■) and data points for the His-Phe are indicated by the symbol (●). FIG. 2a is for the 80% cross-linked polymer P-1, FIG. 2B is for the 70% cross-linked polymer P-2, FIG. 2C is for the 50% cross-linked polymer P-4 and FIG. 2D is for the 30% cross-linked polymer P-6.

Values for $B_{max}$ for these peptides as determined from these isotherms are reported in Table 4. The ratio of the His-Ala $B_{max}$ over the His-Phe $B_{max}$ gives some measure of the selectivity of these polymers in terms of capacity. This ratio is termed , and is shown in Table 4 for each of the polymers discussed.

The isotherm for 80% cross-linked P-1 is shown in FIG. 2A. There is clearly an increased capacity for the smaller template peptide His-Ala over His-Phe. The value for this polymer is 3.3 (Table 4). FIG. 2B contains the isotherms for 70% cross-linked P-2. There is an obvious increase in capacity for both His-Ala and His-Phe associated with decreasing the cross-linking of the polymer by 10%. However, the selectivity of this polymer is somewhat reduced, giving an value of 2.2 (Table 4).

TABLE 4

Maximum binding capacities for His-Ala and His-Phe binding, uptake selectivity and Ni(II) content for P-1 through P-6.

| Polymer | Cross-link (mol %) | $B_{max}$ (mol bound/mol Ni) His-Ala | His-Phe | | Ni content (wt %) Measured | theoretical |
|---|---|---|---|---|---|---|
| P-1 | 80 | 0.44 | 0.13 | 3.3 | 0.51 | 0.76 |
| P-2 | 70 | 0.69 | 0.32 | 2.2 | 0.45 | 0.81 |
| P-3 | 60 | 0.67 | 0.31 | 2.2 | 0.42 | 0.87 |
| P-4 | 50 | 0.83 | 0.41 | 2.0 | 0.42 | 0.93 |
| P-5 | 40 | 0.65 | 0.36 | 1.8 | 0.46 | 1.01 |
| P-6 | 30 | 0.29 | 0.30 | 1.0 | 0.48 | 1.10 |

A similar situation is observed for 50% cross-linked polymer P-4 (FIG. 2C). There is a large increase in capacity for both peptides with a concomitant reduction in (Table 4). Interestingly, by decreasing the cross-linking further to 30% in P-6, the capacity for both peptides drops to extremely low levels (FIG. 2D, Table 4). This also results in a loss of selectivity.

Figure 3:
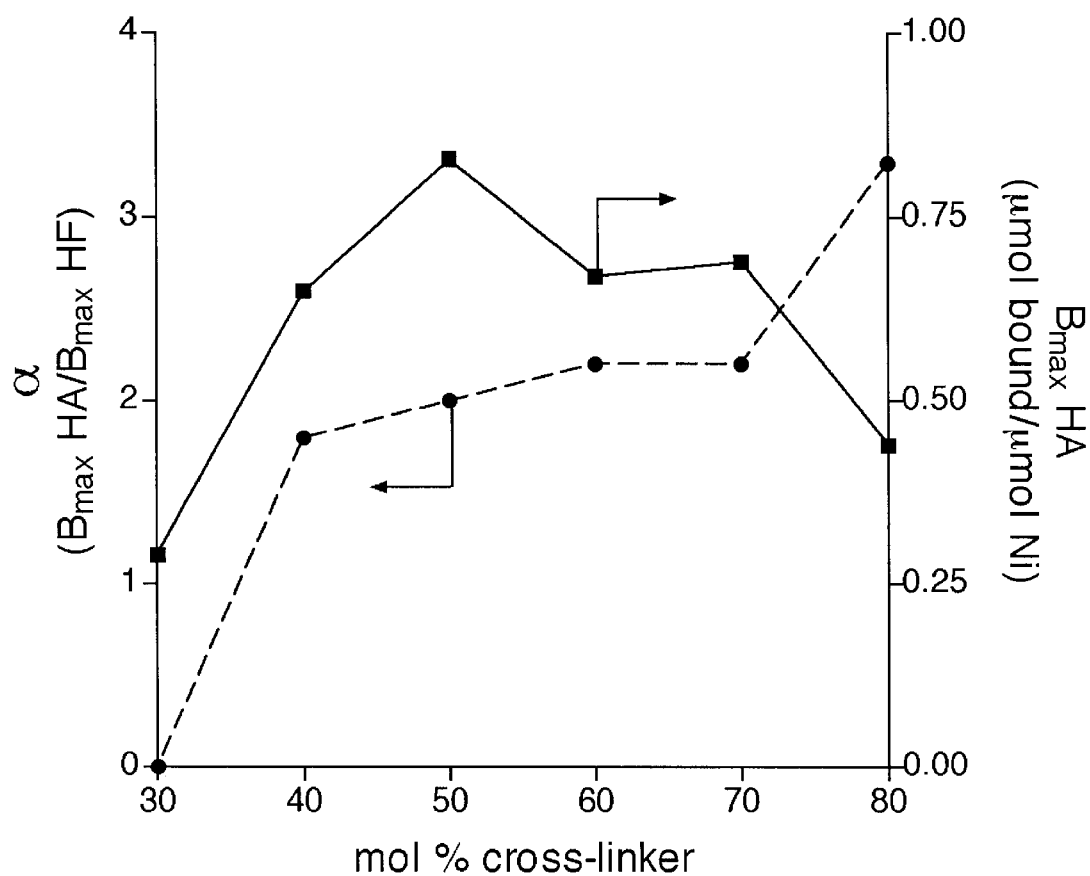
FIG. 3 is a graphic relating the change in (●, left Y axis) and B$_{max}$ HA (■, right Y axis) with mol % cross-linker in a MIP of the present invention.

There is an apparent relationship between cross-link density and both selectivity and absolute capacity for these polymers, as displayed graphically in FIG. 3. The capacity, as represented by $B_{max}$ for His-Ala, is maximized at around 50 mol % cross-linker. The decrease in capacity at the higher cross-linking levels is almost certainly due to inaccessibility of some binding sites. The decrease in uptake at lower levels of cross-linking is not easy to understand. It seems likely that this phenomenon also results from site inaccessibility within the polymer. The cause of this inaccessibility remains unclear and is currently under investigation.

FIG. 3 is a graph showing the change in (●, left Y axis) and $B_{max}$ HA (■, right Y axis) with mol % cross-linker in the polymer. FIG. 3 also indicates that there is a significant dependence of selectivity ( ) on cross-link density. The highest value was obtained with P-1, which has the highest cross-link content of all of the polymers studied. This result is understandable, since th observed selectivity appears to result from a size exclusion type model.

The scope of the size selectivity observed with His-Ala imprinted polymers was further examined by using His-Phe as the template peptide (P-8). The mole fractions of EBA, acrylamide and template complex were identical to P-4 and are shown in Table 5. This polymer formulation was chosen based on the results from the cross-link study that indicated 50 mol % cross-linker provided the highest selectivity. This polymer was prepared and processed in exactly the same manner as polymer P-1 through P-6. The splitting yield was found to be 87%.

TABLE 5

Polymerization formulation composition for the synthesis of EBA cross-linked polymers P-8 and P-9.

| | Polymer Formulation Components (mol %) | | | |
|---|---|---|---|---|
| Polymer | Template Peptide | NTA Complex | Acrylamide | EBA |
| P-8 | His-Phe | 2 | 48 | 50 |
| P-9 | His-(Ala)$_4$ | 2 | 48 | 50 |

Figure 4:
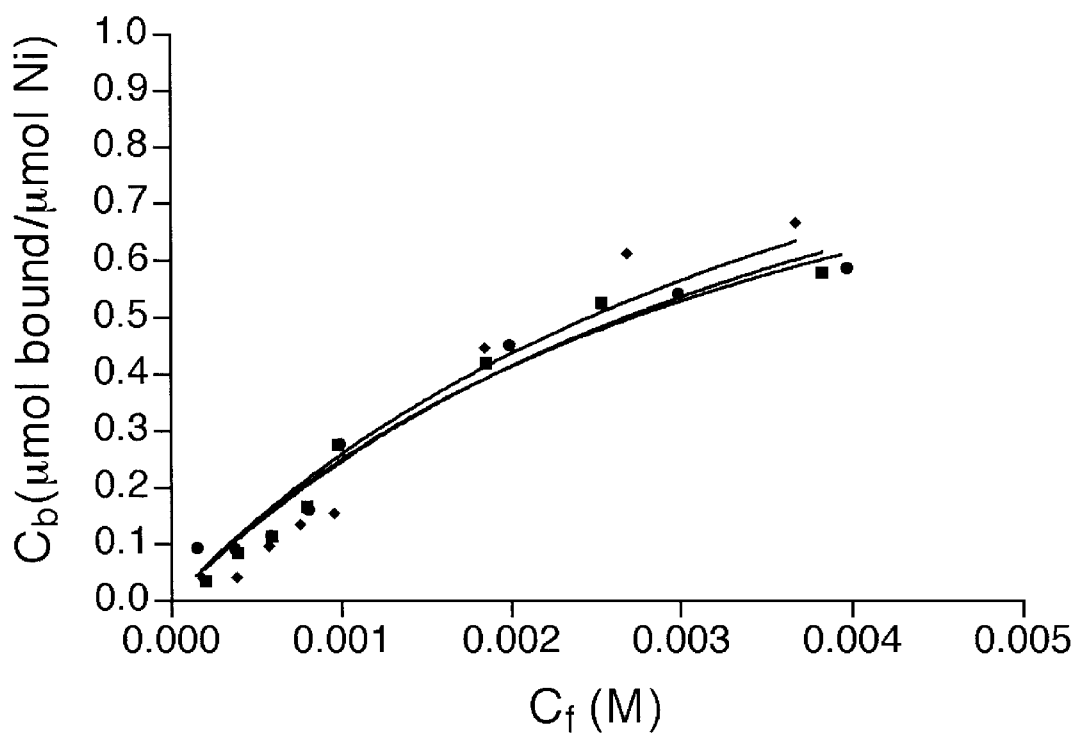
FIG. 4 is a graphic showing isotherms for binding of His-Ala (■), His-Phe (●) and His-Ala-Phe (♦) to a MIP of the present invention.

FIG. 4 shows isotherms for binding of His-Ala (■), His-Phe (●) and His-Ala-Phe (♦) to P-8. Batch rebinding analysis of N-terminal histidine peptides His-Phe, His-Ala and His-Ala-Phe was performed using this polymer. The results were normalized for nickel content as described previously and plotted as $C_b$ ($\mu$mol bound/$\mu$mol Ni) versus $C_f$ (M).

The values for $B_{max}$ His-Ala, His-Phe and His-Ala-Phe are nearly identical for this polymer (0.7 $\mu$mol bound/$\mu$mol Ni, FIG. 4). This observation fits well with the theory that the size of the template plays a large role in determining the rebinding capacity. The larger phenylalanine residue of the template His-Phe results in the polymer maintaining a high rebinding capacity for peptides with small side chains on the second residue. These data also indicates that steric bulk introduced on the third residue (His-Ala-Phe) does not have an effect on the capacity of the polymer. Additionally, these data indicate that there is no inherent difference in affinity of His-Ala over His-Phe or His-Ala-Phe that might have resulted in the previously observed selectivity.

Extension of this methodology to imprint longer peptide sequences may be initiated by imprinting the pentapeptide His-(Ala)$_4$ (P-9). Use of this simple peptide may add steric bulk at positions farther away from the nickel center.

For polymer P-9, the mole fractions of EBA, acrylamide and template complex are substantially the same to P-4 and P-8 and are given in Table 4. In addition, this polymer is prepared and processed in the same manner as described above. The splitting yield for this polymer P-9 is approximately 85%.

Data analysis of N-terminal histidine peptides His-Phe, His-Ala and His-Ala-Phe, His-(Ala)$_4$ and His-Phe-Ala-Ala-Ala may be performed using this polymer. However, due to limited quantities of polymer, full isotherms were not obtained. Instead, single-point binding at high concentrations of peptide were performed. In this way, the maximum binding for each peptide could be determined and compared. The results were normalized for nickel content as described previously and are listed in Table 6.

TABLE 6

Maximum binding ($\mu$mol bound/$\mu$mol Ni) of N-terminal histidine peptides to polymer P-9.

| Peptide Analyte | Maximum Binding ($\mu$mol bound/$\mu$mol Ni) |
|---|---|
| His-Ala | 0.79 |
| His-Phe | 0.77 |
| His-Ala-Phe | 0.65 |
| His-Ala-Ala-Ala-Ala | 0.50 |
| His-Phe-Ala-Ala-Ala | 0.49 |

These results show a clear preference for the binding of smaller peptide substrates to P-9. The dipeptides His-Ala and His-Phe demonstrate the greatest binding per $\mu$mol of nickel. These are followed by the tripeptide His-Ala-Phe. Interestingly the polymer has an almost identical capacity for the template pentapeptide, His-(Ala)$_4$, as it does for His-Phe-Ala-Ala-Ala.

These results are particularly surprising in light of the results from the His-Ala imprinted polymers showing a dramatic decrease in binding for His-Phe. For that system, it appears that additional steric bulk at the second amino acid results in reduced binding to the polymer. However, in the pentapeptide system, binding capacity seems to be more affected by the length of the peptide sequence. There is practically no difference in uptake of peptides with or without a bulky phenylalanine residue at the second position in the sequence.

These observations indicate that there may be a difference in the way the longer peptides effect the environment around the metal complex during the polymerization. The observed results might be expected if the longer peptide template creates, on average, a larger region around the complex that is devoid of polymer chains. The effect might be to reduce the sensitivity of binding to changes in the size of the side chains of the amino acids and, instead, demonstrate selective uptake according to the overall size of the peptide.

Ionic Strength Effects

Initial attempts to perform batch rebinding experiments on these materials using phosphate buffered (30 mM) conditions led to little or no uptake of template dipeptide His-Ala being observed. The difference between buffered and unbuffered experiments was dramatic even with relatively low buffer concentration. Binding was essentially completely inhibited at buffer concentrations as low as 5 mM. In order to explore this effect, a series of buffers was examined for their effect on binding (FIG. 5).

Figure 5:
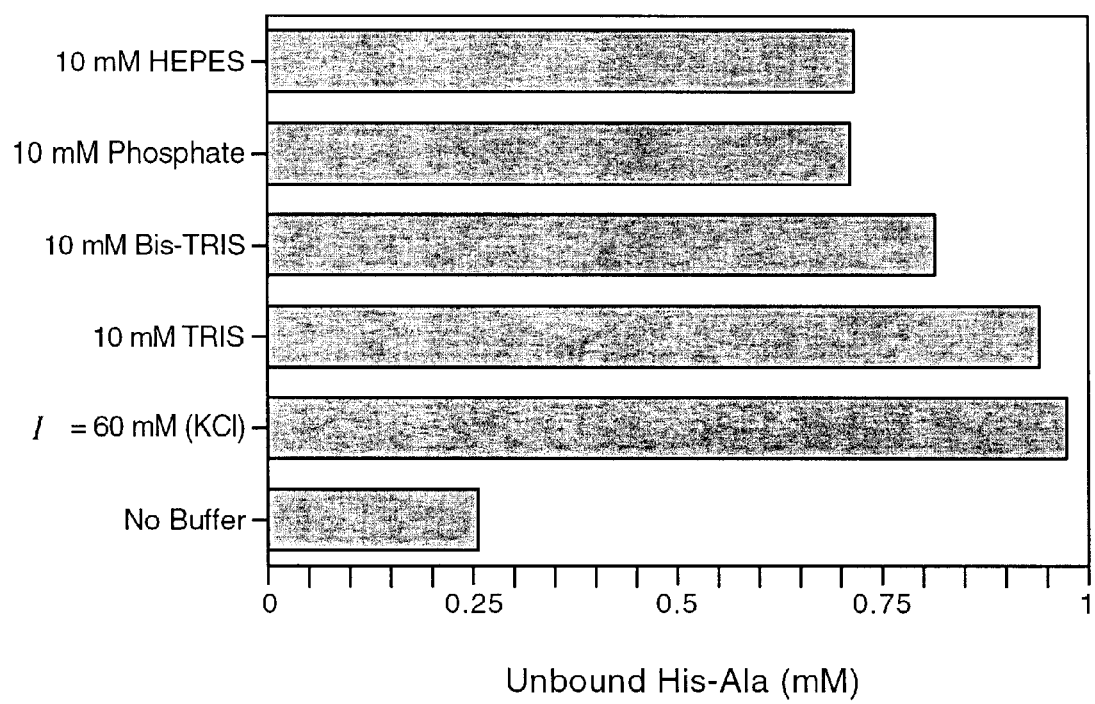
FIG. 5 is a graphic showing the effects of various buffers and ionic strength on peptide uptake by an MIP of the present invention.

FIG. 5 indicates the effect on binding of the presence of a buffer or elevated ionic strength by showing the amount of unbound peptide present at equilibrium. These experiments were performed by incubating 20 mg polymer (P-10, 80% EBA cross-linked polymer prepared using AIBN as the initiator) with various buffered solutions of 1 mM His-Ala. The amount of unbound peptide was measured at equilibrium and plotted in FIG. 5. Also shown in FIG. 5 is the amount of unbound peptide present when unbuffered water was used. Although these experiments were performed using P-10, identical behavior was observed with all polymers.

All buffers resulted in a decrease in peptide uptake. The smallest effect was observed with 10 mM HEPES and 10 mM phosphate buffers. Interestingly, the largest effect was seen in the absence of buffer, but with the ionic strength of the solution adjusted to 60 mM with KCl. This result indicates that the effect is likely due to changes in the ionic strength of the solution caused by the buffers and not directly related to the buffers themselves. It has been shown that the homogeneous [Ni(NTA)HA]⁻ complex is not affected by high ionic strength.[5]

One possible explanation is that the polymer structure itself is affected by the presence of dissolved salts. The solution conformation of high molecular weight, charged and uncharged linear polyacrylamides have been reported to be sensitive to disolved salt.[21] These experiments utilized three commercially available polyacrylamides. One of these (Percol 351, M=20 million) was nonionic, another (Percol 721, M=20 million) was polycationic and another (Percol E-24, M=15 million) was polyanionic. All three of these polymers showed a decrease in the radius of gyration, $<r_g>$, when the concentration of NaCl in solution was raised over a range of 1 mM to 1 M. The largest effect was observed for the polyanionic polymer where the $<r_g>$ was reduced nearly 40%. The largest change in $<r_g>$ for this polymer occurred between 10 and 100 mM NaCl concentration and corresponded to a 30% decrease. This effect has been attributed to coiling of the polymer chains. Another example of electrolyte-sensitive polyacrylamides was observed in polyanionic polyacrylamide gels.[22] In these cases the presence of dissolved salts at concentrations greater than 1 mM brought on a collapse of the gel. In this case the polymer gels were lightly cross-linked (~1 mol %) allowing visual observation of the collapse. These materials were found to shrink to 10–20% of their initial volume.

In both these cases, contraction of the polymer was attributed to shielding of the negative charges within the polymer by the dissolved cations. The result is to reduce the effective ionization of the polymer, causing collapse of the polymer chains. Our system is also polyanionic. There are two possible sources of negative charge within our polymers. The first is the complex itself, which has an overall −1 charge as the aquo-complex and overall −2 when bound to a peptide. In addition, any polymer-bound NTA ligand that is not bound to nickel will have an overall −2 charge at pH 7.5. It is likely that our materials undergo similar phenomena to those reported. The network polymers that were used are much more highly cross-linked than the materials reported by Tanaka. Because of this, no visible change in swelling was observed in the presence of dissolved salts for our materials. However, changes in the microenvironment around the binding sites could cause the observed decrease in peptide uptake.

Kinetic Binding Studies

The kinetics of peptide binding to our polymer-bound Ni(II) complexes was explored. In addition to providing information about the time required to reach equilibrium, these experiments provide another way to determine the value of association constants by experimentally measuring the rates of association and dissociation. In these experiments, dipeptide His-Trp (9) was used as a fluorescent ligand for the polymer-bound complexes. The synthesis of 9 is shown in Scheme 4. Boc group removal from benzyl ester 6[23] was achieved by treatment with TFA. Treatment of bis-CBZ-L-histidine with isobutyl chloroformate and N-ethyl morpholine, followed by addition of 7, gave protected dipeptide 8. Removal of the CBZ and benzyl groups was affected by treatment of 8 with 10% Pd/C and TFA in ethanol under 1 atmosphere of H₂ to give 9.

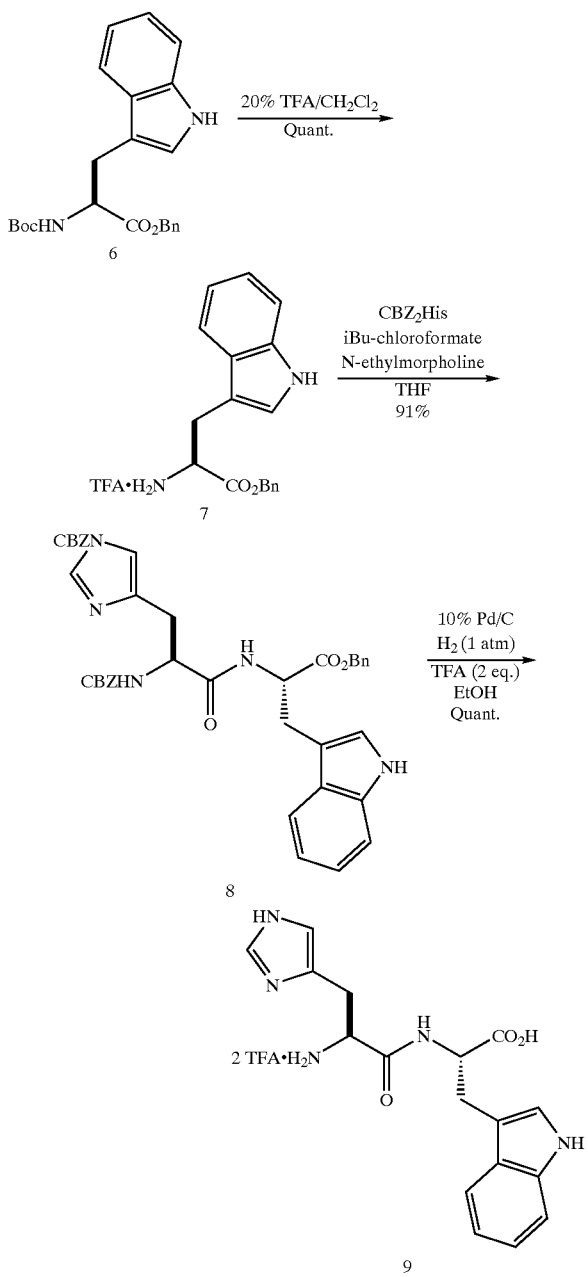

Scheme 4
Solution phase synthesis of dipeptide His-Trp (9).

Absorbance and fluorescence spectra of 9 were obtained and it was found to have an absorbance$_{max}$ of 278 and a fluorescence$_{max}$ of 365. Tryptophan alone has an absorbance$_{max}$ of 280 and a fluorescence$_{max}$ of 348.[24] A fluorescence calibration curve was prepared for determining the concentration of 9 in solution. Two types of experiments, association and dissociation, were performed to measure $k_1$ and $k_{-1}$, for the binding of His-Trp to the polymer.

Association experiments were performed by adding a solution of 9 (140 M) to P-4 (10 mg) and monitoring the fluorescence of the supernatant solution. The concentration of unbound peptide ($C_f$) in the supernatant was determined by reference to the calibration curve. The concentration of ligand bound to the polymer, $C_b$, was calculated as described and plotted versus time as shown in FIG. 6.

Figure 6:
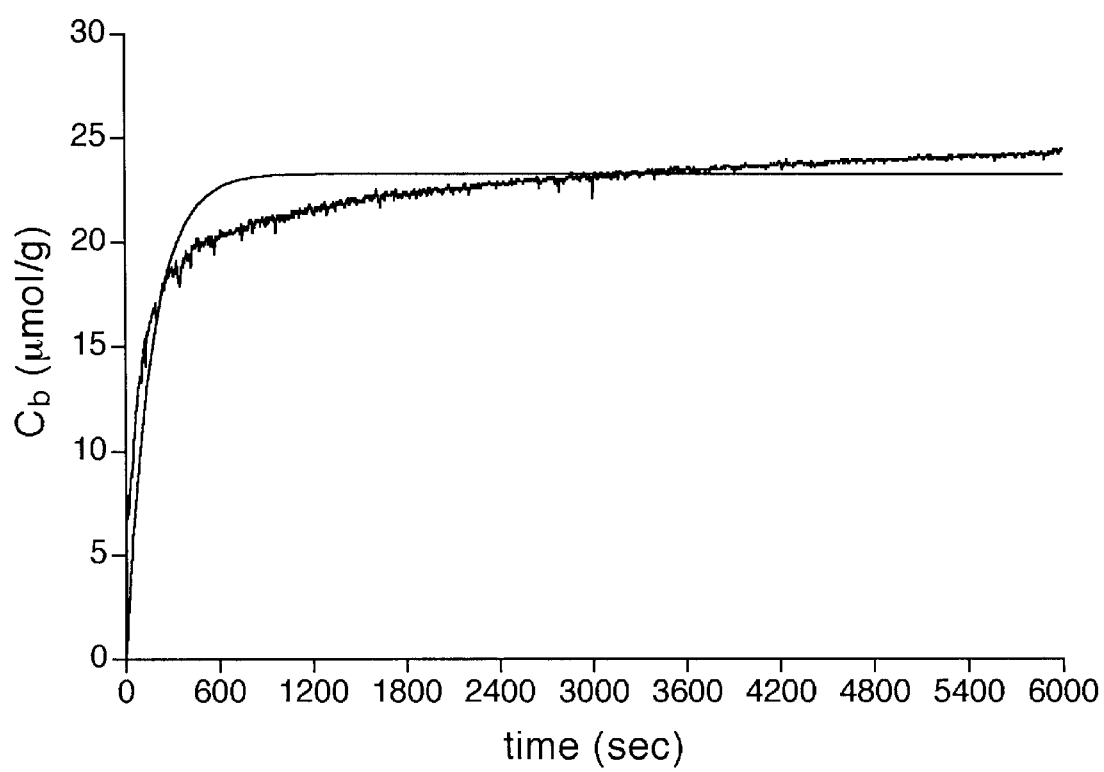
FIG. 6 is a graphic showing bound His-Trp versus time for association of peptide to a MIP of the present invention and best fit line describing the association according to an exponential association expression.

FIG. 6 is a plot of bound His-Trp (9) versus time for association of peptide to polymer P-4 (jagged line) and best fit line describing the association according to an exponential association expression (smooth line). As shown, binding increases over time until it plateaus at $Y_{max}$ at 23 mol/g. This value represents the amount of binding at equilibrium with this specific concentration of peptide in solution. It is different from $B_{max}$, which is the amount of binding extrapolated to a very high concentration of ligand. The kinetics of association are defined by a one-phase exponential association. By fitting the data from the association experiment to this equation, we obtained a value for the observed rate constant, $k_{ob}$, of 5.88 $10^{-3} \pm 5\ 10^{-4}\ sec^{-1}$.

The association data in FIG. 6 deviates somewhat from the best fit line; most notably, where the curve begins to level. This deviation may be due to the fact that we are observing association in a heterogeneous system. After the readily accessible sites within the polymer become saturated, mass transport begins to limit the rate at which molecules are adsorbed by the material. This has the effect of greatly increasing the uncertainty in the value of $k_{ob}$.

Dissociation experiments were performed by incubating polymer P-4 with a solution of His-Trp (140 M) until equilibrium had been reached. The supernatant solution was removed from the polymer followed by addition of water. Release of bound peptide was monitored by fluorescence and the value of $C_b$ was calculated as before and plotted versus time as shown in FIG. 7.

Figure 7:
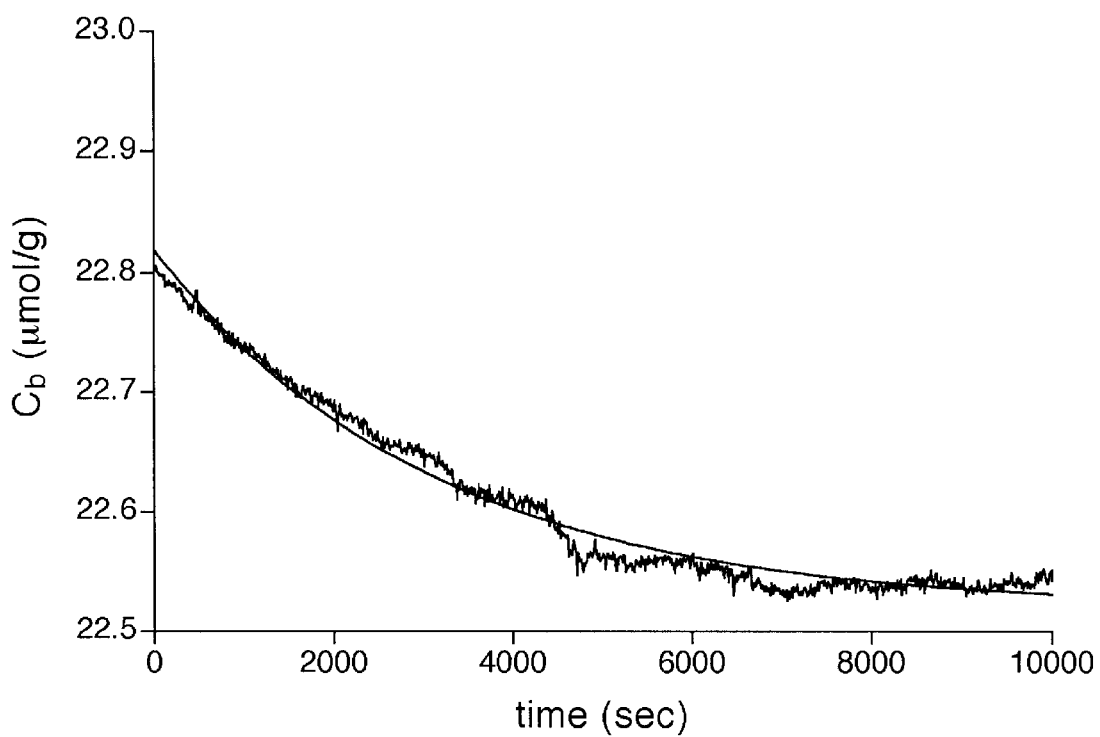
FIG. 7 is a graphic showing bound His-Trp versus time for dissociation of peptide from a MIP of the present invention and best fit line describing the dissociation according to an exponential decay expression.

FIG. 7 is a plot of bound His-Trp (9) versus time for dissociation of peptide from polymer P-4 (jagged line) and best fit line describing the dissociation according to an exponential decay expression (smooth line).

Ideally, the concentration of peptide after dilution with fresh solvent should be well below the $K_d$ for the association. However, this system is limited by the sensitivity of the fluorescence technique due to the relatively small quantum yield of tryptophan (=0.2). This requires us to have a fairly high concentration of His-Trp. Because of this, there is competition between association and dissociation so the rate measured is not simply the dissociation rate, but an approach to equilibrium. However, by fitting this data to an exponential decay equation we are able to obtain an observed rate of dissociation ($k_{off}$) of 3.21 $10^{-4} \pm 4\ 10^{-6}\ sec^{-1}$.

The results of these kinetic binding studies indicate that these materials rebind N-terminal histidine peptide substrates with an observed rate constant of 5.88 $10^{-3} \pm 5\ 10^{-4}\ sec^{-1}$. This allows for equilibration times of under 1 hr for these systems. In addition, the high affinity of these peptides for the polymer-bound complexes is reflected in very slow dissociation rates. In the future, it may be possible to perform this experiment using a peptide tagged with a more highly fluorescent probe than simply tryptophan, thus, allowing a more accurate determination of $k_{off}$. It is also important to point out that the data obtained with these experiments pertains to the binding of His-Trp, which may be able to interact with the polymer in ways the previous peptides did not.

As may be appreciated from the description provided above, the present invention provides methods for creating macromolecular receptors for peptides using molecular imprinting. The use of water in the polymer synthesis and recognition steps has obvious advantages over organic systems. The use of N,N'-ethylenebisacrylamide as cross-linking monomer provides good water solubility and can be used to create highly cross-linked polyacrylamides with good stability. The present invention also provides a polymerizable NTA ligand, which can be used to incorporate nickel and other metals into these polyacrylamides. Polymerization conditions have been developed, which allow initiator concentration and temperature to be extremely low while maintaining quantitative polymer yields.

Preparation of Reagents and Experimental Methods

The following are examples of methods for preparing certain reagents used in the synthesis of MIPs according to this invention. It is to be appreciated, however, that alternative methods of preparing the same reagents may be available. Also provided herebelow are descriptions of the methodology used in the tests, assays and studies referred to hereabove.

N-Benzyloxycarbonyl-N-bis(2-ethoxy-2-oxoethyl)-L-lysine methyl ester (2). To a solution of N-benzyloxycarbonyl-L-lysine methyl ester (1.0 g, 3.4 mmol) in acetonitrile (25 mL) was added ethylbromoacetate (5.68 g, 34 mmol) followed by finely ground $K_2CO_3$ (9.4 g, 68 mmol). The reaction mixture was heated at reflux for 18 h. The reaction mixture was filtered through Celite and concentrated. Flash column chromatography of the resulting oil using hexanes to elute the residual ethylbromoacetate followed by 2:1 hexanes/EtOAc provided triester 2 as a colorless oil (1.300 g, 82%). $^1$H NMR (CDCl$_3$) 7.30 (m, 5H), 5.08 (s, 2H), 4.94 (br s, 1H), 4.11 (q, J=7.1 Hz, 4H), 3.7 (s, 3H), 3.41 (d, J=17.6 Hz, 2H), 3.58 (d, J=17.6 Hz, 2H), 3.19 (m, 2H), 1.69 (m, 2H), 1.52 (m, 2H), 1.39 (m, 2H), 1.23 (t, J=7.1 Hz, 6H) ppm; $^{13}$C NMR (CDCl$_3$) 173.1, 171.4, 156.4, 136.7, 128.5, 128.1, 128.0, 66.5, 64.5, 60.6, 52.6, 51.4, 40.7, 29.9, 29.3, 22.9, 14.2 ppm; IR (Neat) 3380, 2950, 1732, 1526 cm$^{-1}$; HRMS calcd for $C_{23}H_{35}N_2O_8$ (M+H)$^+$ 467.2393 found 467.2401; [ ]$^{25}_D$=-23.0 (c=1.05, ethanol).

N-(2-methyl-1-oxopropenyl)-N-bis(2-ethoxy-2-oxoethyl)-L-lysine methyl ester (3). To a solution of 2 (0.97 g, 1.90 mmol) in ethanol (50 mL) was added 10% Pd/C (10 mg). This solution was stirred vigorously under $H_2$ (1 atm) for 2 h until no starting material could be seen by TLC (3:2 EtOAc/hexanes). The reaction mixture was filtered through Celite and concentrated in vacuo. The resulting residue was dissolved in THF (50 mL). To this solution was added triethyl amine (0.53 mL, 3.8 mmol) followed by dropwise addition of methacryloyl chloride (0.19 mL, 1.9 mmol) in THF (10 mL). The reaction was stirred for 30 min at 0° C. then 8 h at 25° C. The mixture was concentrated. Flash column chromatography of the resulting oil (1:1 EtOAc/hexanes) provided methacrylamide 3 as a colorless oil (0.350 g, 46%). $^1$H NMR (CDCl$_3$) 6.14 (br s, 1H), 5.67 (s, 1H), 5.27 (s, 1H), 5.10 (q, J=7.1 Hz, 4H), 3.65 (s, 3H), 3.61 (d, J=17.7 Hz, 2H), 3.57 (d, J=17.7 Hz, 2H), 3.40 (t, J=8.2 Hz, 1H), 3.27 (m, 2H), 2.01 (s, 3H), 1.68 (m, 2H), 1.60–1.40 (m, 4H), 1.23 (t, J=7.1 Hz, 6H) ppm; $^{13}$C NMR (CDCl$_3$) 173.1, 171.3, 168.5, 140.1, 119.7, 64.3, 60.5, 52.6, 51.4, 39.3, 29.7, 28.6, 23.0, 18.6, 14.1 ppm; IR (Neat) 3348, 2935, 1738, 1729 cm$^{-1}$; HRMS calculated for $C_{19}H_{33}N_2O_7$ (M+H)$^+$ 401.2288 found 401.2289; [ ]$^{23}_D$=27.2 (c=0.80, ethanol).

N-(2-methyl-1-oxopropenyl)-N-bis(carboxymethyl)-L-lysine trilithium salt (4). To a solution of 3 (2.4 mmol) in 25% $H_2O$/acetone (30 mL) was added LiOH (7.2 mmol). The reaction was stirred at room temperature for 12 h. Acetone was removed in vacuo and the resulting aqueous solution was lyophilized to give 4 as a white solid (quantitative yield). mp >300° C.; $^1$H NMR (D$_2$O) 5.52 (s, 1H), 5.29 (s, 1H), 3.13 (ddd, J=6.8, 6.8, 2.6 Hz, 2H), 3.03 (d, J=17.0 Hz, 2H), 2.95 (d, J=17.0 Hz, 2H), 2.89 (dd, J=8.6, 5.5 Hz, 1H), 1.79 (s, 3H), 1.56 (m, 2H), 1.43 (m, 2H), 1.33–1.20 (m, 2H) ppm; $^{13}$NMR (D$_2$O) 181.7, 180.4, 171.3, 138.6, 119.8, 67.3, 56.2, 38.6, 27.7, 27.5, 23.7, 17.0 ppm; IR (KBr) 3396, 2940,1592,1413 cm$^{-1}$.

Trp-OBn.TFA (7). N-Boc-L-tryptophan benzyl ester (0.5 g, 1.27 mmol) was dissolved in a solution of 20% TFA in $CH_2Cl_2$. The reaction mixture was stirred under nitrogen at room temperature for 30 min and evaporated to dryness. Trituration of the resulting oil with $Et_2O$ provided 7 as a white solid (quantitative yield). mp=143–145° C.; $^1H$ NMR ($CD_3CN$) 9.42 (br s, 1H), 7.51 (d, J=8.0 Hz, 1H), 7.43 (d, J=8.2 Hz, 1H), 7.35 (m, 3H), 7.26 (m, 2H), 7.16 (m, 2H), 7.04 (t, J=7.9 Hz, 1H), 5.15 (d, J=12.3 Hz, 1H), 5.09 (d, J=12.3 Hz, 1H), 4.36 (t, J=6.2 Hz, 1H), 3.44 (d, J=6.2 Hz, 2H) ppm; $^{13}C$ NMR ($CDCl_3$) 170.1, 137.6, 136.0, 129.5, 129.4, 129.3, 128.1, 126.2, 122.9, 120.3, 119.1, 112.6, 107.5, 68.8, 54.4, 26.9 ppm; IR (KBr) 3412, 2840, 1742, 1673, 1498, 1205, 1137, 735 $cm^{-1}$; HRMS calcd for $C_{18}H_{19}N_2O_2$ 294.1368 found 294.1362.

CBZ-His(CBZ)-Trp-OBn (8). To a solution of CBZ-L-His(CBZ)-OH (0.136 g, 0.32 mmol) and N-ethyl morpholine (32 L, 0.25 mmol) in THF (1 mL) and DMF (0.1 mL) at −18° C. was added i-butyl chloroformate (42 L, 0.32 mmol). After an activation period of 10 min a solution of 7 (0.100 g, 0.25 mmol) and N-ethyl morpoholine (42 L, 0.33 mmol) in THF (1 mL) was added dropwise. The reaction mixture was stirred under nitrogen at −18° C. for 1 h then overnight at room temperature. The reaction mixture was cooled to 0° C. followed by addition of $NaHCO_3$ (1 mL, 5% aqueous solution). After 10 min this solution was warmed to room temperature and diluted with EtOAc (5 mL). The aqueous layer was removed and washed 1 with 5 mL EtOAc. The organics were combined and washed 3 with 10 mL 1 N HCl, dried over $Na_2SO_4$ and concentrated. The residue was purified by flash column chromatography (70% EtOAc/haxanes) to provide 8 as a white solid (0.159 g, 91%). mp=62–64° C.; $^1H$ NMR ($CDCl_3$) 8.08 (br s, 1H), 7.94 (br s, 1H), 7.43 (m, 6H), 7.31 (m, 12H), 7.10 (m, 2H), 7.01 (m, 1H), 6.79 (br s, 1H), 6.45 (br d, J=6.6 Hz, 1H), 5.34 (d, J=12.0 Hz, 1H), 5.31 (d, J=12.0 Hz, 1H), 4.88–5.11 (m, 5H), 4.60 (br s, 1H), 3.23 (br m, 2H), 3.00 (dd, J=14.8, 5.2 Hz, 1H), 2.92 (dd, J=14.8, 5.2 Hz, 1H) ppm; $^{13}C$ NMR ($CDCl_3$) 171.3, 170.6, 156.14, 147.9, 138.3, 136.5, 136.3, 135.9, 135.2, 133.7, 129.2, 128.8, 128.7, 128.6, 128.5, 128.4, 128.3, 128.2, 128.1, 127.3, 123.3, 121.9, 119.4, 118.4, 114.9, 111.1, 109.2, 70.0, 67.0, 66.9, 54.5, 52.6, 29.7, 27.4 ppm; IR (KBr) 3347, 3034, 2927, 1752, 1734, 1670, 1405, 1247, 1012, 742, $cm^{-1}$; HRMS submitted.

His-Trp.2 TFA (9). To a solution of 8 (0.089 g, 0.127 mmol) and TFA (35 L) in EtOH (20 mL) under nitrogen was added 10% Pd/C (10 mg). This solution was stirred under $H_2$ (1 atm) overnight. The reaction mixture was filtered through Celite and evaporated to dryness. Trituration of the resulting oil with $Et_2O$ provided 9 as a white solid in quantitative yield. Dec. 137–142° C.; $^1H$ NMR (DMSO-$d_6$) 10.64 (s, 1H), 8.61 (br s, 1H) 8.06 (s, 1H), 7.52 (d, J=7.8 Hz, 1H), 7.32 (d, J=7.9 Hz, 1H), 7.06 (m, 2H), 6.97 (m, 1H), 6.87 (s, 1H), 4.59 (br s, 1H), 4.08 (dd, J=7.3, 5.7 Hz, 1H), 3.20 (dd, J=14.7, 5.7 Hz, 1H), 3.04 (dd, J=14.7, 8.0 Hz, 1H), 2.95 (dd, J=15.4, 5.3 Hz, 1H), 2.82 (dd, J=15.4, 7.6 Hz, 1H) ppm; $^{13}C$ NMR (DMSO-$d_6$) 172.7, 167.5, 139.9, 136.1, 137.8, 127.0, 123.8, 121.0, 118.4, 118.1, 116.1, 111.4, 109.3, 53.1, 51.9, 27.7, 27.3 ppm; IR (KBr) 3421, 3144, 3048, 2934, 1676, 1651, 1205, 837, 723 $cm^{-1}$; HRMS $C_{17}H_{20}N_5O_3$ $(M+H)^+$ 342.1566 found 342.1554.

Boc-Ala-Phe-OMe. To a solution of Boc-Ala-OH (0.50 g, 2.64 mmol) and N-ethyl morpholine (0.336 mL, 2.64 mmol) in THF (10 mL) at −18° C. was added i-butyl chloroformate (0.317 mL, 2.44 mmol). After an activation period of 10 min a solution of Phe-OMe (0.406 g, 1.88 mmol) and N-ethyl morpoholine (0.240 mL, 1.88 mmol) in DMF (4 mL) was added dropwise. The reaction mixture was stirred under nitrogen at −18° C. for 1 h then overnight at room temperature. The reaction mixture was cooled to 0° C. followed by addition of $NaHCO_3$ (10 mL, 5% aqueous solution). After 10 min this solution was warmed to room temperature and diluted with EtOAc (5 mL). The aqueous layer was removed and washed 2 with 20 mL EtOAc. The organics were combined and washed 3 with 10 mL 1 N HCl, dried over $Na_2SO_4$ and concentrated. The residue was purified by flash column chromatography (70% EtOAc/haxanes) to the product as a white solid (0.159 g, 91%). $^1H$ NMR ($CDCl_3$) 7.31 (m, 3H), 7.14 (m, 2H), 6.63 (d, J=7.4 Hz, 1H), 5.05 (br s, 1H), 4.87 (q, J=6.9 Hz, 1H), 4.18 (br s, 1H), 3.73 (s, 3H), 3.18 (dd, J=13.9, 6.1 Hz, 1H), 3.10 (dd, J=13.9, 5.8 Hz, 1H), 1.46 (s, 9H), 1.33 (d, J=6.9 Hz, 3H); $^{13}C$ NMR ($CDCl_3$) 172.2, 171.7, 155.3, 135.7, 129.2, 128.5, 127.1, 80.0, 53.1, 52.3, 50.0, 37.8, 28.2, 18.2; IR (KBr) 3315, 2978, 1744, 1708, 1666, 1522, 1453, 1366,1168; HRMS calcd for $C_{18}H_{27}N_2O$ $(M+H)^+$ 351.1920 found 351.1916.

His-Ala-Phe.2TFA. To a solution of Boc-Ala-Phe-OMe (0.43 g, 0.73 mmol) in 25% $H_2O$/acetone was added LiOH (0.044 g, 0.73 mmol). The reaction was stirred at room temperature for 12 h. Acetone was removed in vacuo and the resulting aqueous solution was lyophilized to give a white solid. This solid was dissolved in 1:5 TFA/$CH_2Cl_2$ (15 mL) and stirred under nitrogen for 1 h. The reaction mixture was concentrated in vacuo. Trituration of the resulting oil with $Et_2O$ provided the product as a white solid (0.221 g, 81%). Dec. 160° C.; $^1H$ NMR ($D_2O$) 8.30 (s, 1H), 7.22 (m, 3H), 7.17 (m, 2H), 7.10 (s, 1H), 4.37 (m, 1H), 4.23 (q, J=7.2 Hz, 1H), 4.13 (m, 1H), 3.20 (dddd, J=12.3, 12.3, 12.3, 5.7 Hz, 2H), 3.07 (dd, J=14.0, 5.3 Hz, 1H), 2.90 (dd, J=14.0, 8.6 Hz, 1H), 6.50 (d, J=7.2 Hz, 3H) ppm; 13C NMR ($CD_3OD$) 175.4,174.8, 168.8, 138.6, 136.3, 130.6, 129.6, 128.8, 120.0, 55.9, 53.3, 50.9, 38.4, 28.2, 18.0 ppm; IR (KBr) 3419, 3040, 2670, 1681, 1558, 1437, 1205, 1139, 704; HRMS submitted.

Batch binding studies. Stock solutions of the peptide to be analyzed (2.0–7.0 mM) were prepared in distilled, deionized $H_2O$. Serial dilutions of these solutions provided stock solutions between 0.05 and 7.0 mM. The pH of these solutions was adjusted to pH 7.5 with 0.1 N KOH. 0.50 mL of each stock solution was added to 1 mL HPLC autoinjector vials containing either no polymer or swelled polymer (30 or 60 mg). The vials were shaken overnight at room temperature. The pH of the binding solutions was measured after equilibration to ensure that it did not change. The concentration of unbound analyte, $C_f$, in the supernatant was determined by HPLC (by reference to a calibration curve) on a C18 (Waters Nova-Pak) 3.9×300 mm column. HPLC conditions were 100% mobile phase A for histidine, phenylalanine, and His-Ala and 90:10 A/B for His-Phe, His-Ala-Phe, His-(Ala)$_4$, His-Phe-(Ala)$_3$ and Ala-Phe. After binding, the polymer was washed with MeOH, dried in vacuo and weighed to determine its dry weight. The concentration of ligand bound to the polymer, $C_b$, was calculated as described in Equation 2.4. Data analysis was performed using GraphPad Prism 3.0 software.

Kinetic association experiments. To a heterogeneous mixture of P-4 in 0.5 mL of distilled, deionized $H_2O$ in a fluorescence cuvette was added a solution of His-Trp (9, 0.14 µmol) in distilled, deionized $H_2O$ (0.5 mL) with slow stirring. The fluorescence of the supernatant solution was measured once/sec at 365 nm with an excitation wavelength of 280 nm. The concentration of unbound peptide ($C_f$) in the supernatant was determined by reference to the calibration curve. The concentration of ligand bound the polymer, $C_b$, was calculated as described in Equation 2.4 and plotted versus time.

Kinetic dissociation Experiments. Dissociation experiments were performed by incubating polymer P-4 with a solution of His-Trp (0.14 µmol) in distilled, deionized H$_2$O (1 mL) until equilibrium in a fluorescence cuvette. The supernatant solution was removed from the polymer followed by addition of distilled, deionized H$_2$O (1 mL). Release of bound peptide was monitored by fluorescence as described for the association experiment.

Polymer Synthesis. To Ni(SO$_4$).6H$_2$O (0.021 g, 0.08 mmol) in H$_2$O (0.167 mL) was added peptide template (0.08 mmol) in H$_2$O (0.100 mL). To this solution was added NTA monomer 4 (0.028 g, 0.08 mmol) in H$_2$O (0.167 mL). The pH of this solution (pH paper) was adjusted to 7.5–8.0 using 1 N KOH followed by addition of H$_2$O to bring the total volume to 0.5 mL.

TABLE 7

Amounts (mmol and g) of EBA and acrylamide used to prepare polymers P-10 through P-21 and P-22 based on mol % cross-linker.

| Polymer | mol % cross-linker | EBA | Acrylamide |
|---|---|---|---|
| P-1 | 80 | 3.20 mmol, 0.538 g | 0.72 mmol, 0.051 g |
| P-2 | 70 | 2.80 mmol, 0.470 g | 1.12 mmol, 0.08 g |
| P-3 | 60 | 2.35 mmol, 0.395 g | 1.57 mmol, 0.111 g |
| P-4 | 50 | 2.00 mmol, 0.336 g | 1.92 mmol, 0.136 g |
| P-5 | 40 | 1.57 mmol, 0.264 g | 2.35 mmol, 0.167 g |
| P-6 | 30 | 1.20 mmol, 0.202 g | 2.72 mmol, 1.930 g |
| P-7 | 10 | 0.40 mmol, 0.67 g | 3.52 mmol, 0.250 g |

Ethylenebisacrylamide (see Table 7) and acrylamide (see Table 7) were dissolved in distilled, deionized and O$_2$ free H$_2$O (1 mL) with gentle warming in a 1 dram vial. To this solution was added the complex solution described above followed by a solution of TMEDA (0.35 µmol) and ammonium persulfate (1.8 µmol) in H$_2$O (20 µL). This mixture was purged with nitrogen gas then the vial was sealed and heated with an oil bath at 40° C. for 24 h. The resulting blue monolith was ground and washed with water pH 3–4 to remove the template. Then washed with H$_2$O (pH=7.0, 50 mL). Removal of template was monitored by HPLC and the splitting yield was calculated by combining the washings and quantifying by HPLC. The particles were sieved to isolate the particles between 38 and 425 m.

Potentiometric Titrations. All solutions were made with distilled, deionised and carbon dioxide-free water. His-Ala and Ni(NO$_3$)$_2$.5H$_2$O were purchased from Sigma and Aldrich respectively. NTA monomer 4 was synthesized as described. The KOH solutions (1.00 N) were standardized against potassium hydrogenophthalate. In all experiment, the ionic strength was maintained at 0.100 with KNO$_3$ as the supporting electrolyte.

Potentiometric titrations were carried out using 1.00 N KOH (saturated with N$_2$) with continuous magnetic stirring and under N$_2$ in a 10 mL jacketed vessel at 25.0±0.1° C. The vessel was equipped with a gas tight cap and fitted with gas inlet and outlet tubes, pH electrode and manual piston burette. Titrations of His-Ala, 1:1 NTA monomer/Ni(II) and 1:1:1 His-Ala/Ni(II)/NTA monomer were performed. The solution for titration of the 1:1:1 mixed complex was prepared by dissolving 0.10 mmol of each component in 0.1 M KNO$_3$ solution. The NTA monomer and Ni(II) solutions were combined and transferred to the titration vessel under nitrogen. To this solution was added the His-Ala solution followed by dilution of the mixture to 10 mL. The 1:1 NTA monomer/Ni(II) and His-Ala titration solutions were prepared in a similar manner. All titrations were made after stabilization of the first pH value which was achieved by successive addition of 1.0 M HNO$_3$ to ensure that the titrations would start from a pH value under 2.5. These solutions were titrated with 1.0 M KOH by addition of 0.02 mL and 0.01 mL of titrant. The corresponding pH was read and plotted to calculate the values of the overall formation constants of the systems.

All equilibrium constants were calculated using the computer program Best 7. All mathematical details have been previously described.[14-18] Species distribution curves were obtained from the computer program SPE.

While this invention has been described hereabove with reference to specific examples and embodiments, it is to be understood that the invention is not limited to just these specific embodiments and examples, and that the invention can be variously practiced within the scope of the following claims

What is claimed is:

1. A method for preparing a molecularly imprinted polymer wherein the template comprises a peptide or amino acid sequence having an N-terminal histidine residue or histamine, said method comprising the steps of:

(A) providing a template complex that has the general formula

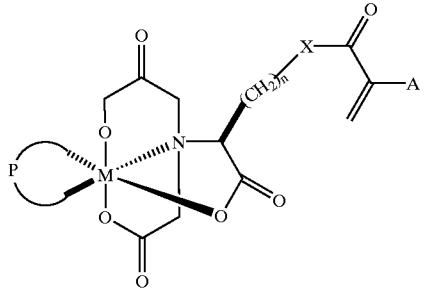

wherein M is nickel, cobalt, copper, zinc, lead or manganese, P is a template peptide or amino acid sequence having at least one N-terminal histidine or a histamine molecule, n=0 through 10, X is NH, O, S or is absent and A is H or alkyl;

(B) polymerizing the template complex provided in Step A with at least a first monomer and optionally said first monomer and a second monomer, to form a polymer network containing the template complex;

the first monomer having the general formula

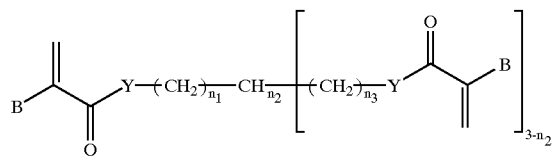

wherein Y is NH, O or S or is absent, $n_1$=0 through 10, $n_2$=0 through 2, $n_3$=0 through 10 and B is H or alkyl and the second monomer, if used, having the general formula

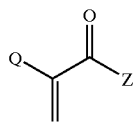

wherein Z=NH$_2$, OH, O—(CH$_2$)$_n$ wherein n=2 through 4, NH(alkyl) or N(alkyl)$_2$ and Q is H or alkyl.

2. A method according to claim 1 further comprising the step of: (C) removing the template complex from the polymer network.

3. A method according to claim 1 wherein the first monomer and any second monomer are water soluble at the concentrations used in the method.

4. A method according to claim 1 wherein the template complex provided in Step A is prepared by combining a polymerizable methacrylamide-NTA—Ni$^{2+}$ complex with a peptide or an amino acid sequence having at least one N-terminal histidine.

5. A method according to claim 4 wherein polymerizable methacrylamide-NTA—Ni$^{2+}$ complex is prepared by reacting NTA with NiSO$_4$.

6. A method according to claim 1 wherein the first monomer comprises N,N'-ethylene bisacrylamide.

7. A method according to claim 1 wherein the first monomer comprises N,N'-methylene bisacrylamide.

8. A method according to claim 1 wherein the second monomer comprises acrylamide.

9. A method according to claim 1 wherein the second monomer comprises methacrylamide.

10. A method according to claim 1 wherein Step B comprises combining about 1–15 mol % of the template complex provided in Step A with about 30–82 mol % of the first monomer and about 0–68 mol % of the second monomer.

11. A method according to claim 1 wherein Step B comprises combining about 1–15 mol % of the template complex provided in Step A with about 30–82 mol % of a first monomer selected from the group consisting of N,N'-ethylene bisacrylamide and N,N'-methylene bisacrylamide, and about 0–68 mol % of the second monomer selected from the group consisting of acrylamide and methacrylamide.

12. A method according to claim 1 wherein Step B comprises combining about 5 mol % of the template complex provided in Step A with about 82 mol % N,N'-ethylene bisacrylamide and about 13 mol % acrylamide.

13. A method according to claim 10 wherein the first monomer and any second monomer are water soluble at the concentrations used in the method and are in aqueous solution during the performance of at least Step B.

14. A method according to claim 2 wherein Step C comprises contacting the polymer prepared in Step B with an acid solution.

15. A method for adsorbing a target compound comprising a predetermined amino acid sequence having at least one N-terminal histidine, said method comprising i) providing a molecularly imprinted polymer prepared according to the method of claim 1 wherein the wherein the amino acid sequence used to prepare the template complex in Step A is the predetermined amino acid sequence and ii) contacting of the molecularly imprinted polymer with the material such that the target compound contained in the material will be adsorbed by the molecularly imprinted polymer.

16. A method for determining whether a material contains a target compound comprising a predetermined amino acid sequence having at least one N-terminal histidine, said method comprising i) providing a molecularly imprinted polymer that has been prepared according to the method of claim 1 wherein the wherein the amino acid sequence used to prepare the template complex in Step A is the predetermined amino acid sequence, ii) contacting the molecularly imprinted polymer with the material such that any substantial quantity of target compound within the material will be adsorbed by the molecularly imprinted polymer and, thereafter, iii) determining whether the molecularly imprinted polymer has adsorbed any of the target compound.

17. A molecularly imprinted polymer prepared by a method according to claim 1.

18. A molecularly imprinted polymer prepared by a method according to claim 2.

* * * * *

UNITED STATES PATENT AND TRADEMARK OFFICE
CERTIFICATE OF CORRECTION

PATENT NO. : 6,525,154 B1
DATED : February 25, 2003
INVENTOR(S) : Shea et al.

It is certified that error appears in the above-identified patent and that said Letters Patent is hereby corrected as shown below:

<u>Column 1,</u>
Line 6, please add the following after the first paragraph and prior to "Field of The Invention":
-- STATEMENT REGARDING FEDERALLY SPONSORED RESEARCH
This invention was made with Government support under Grant No. GM-48400, awarded by the National Institutes of Health. The Government may have certain rights in this invention. --

Signed and Sealed this

Twenty-fourth Day of February, 2004

JON W. DUDAS
*Acting Director of the United States Patent and Trademark Office*